Figure 1:
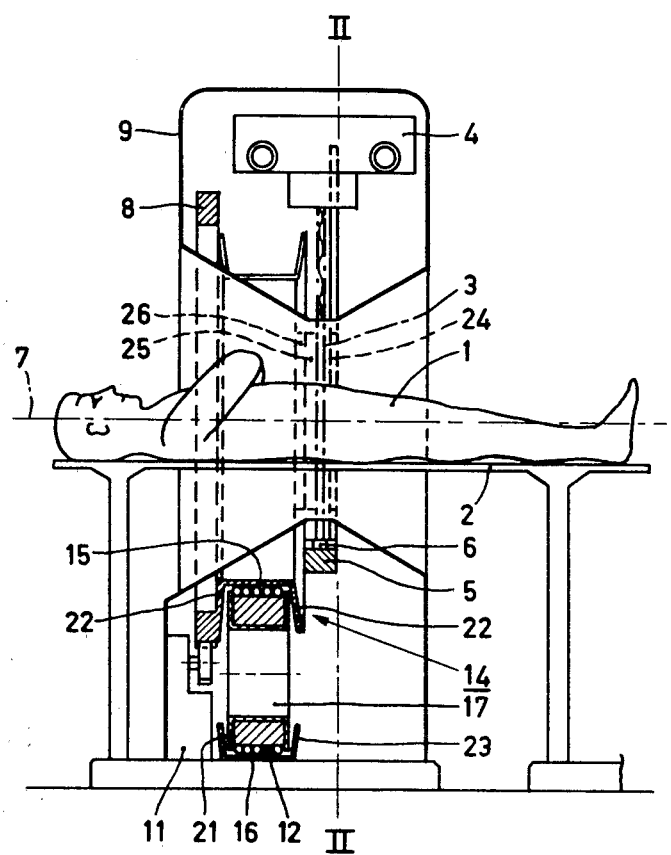

United States Patent [19]

Kuipers

[11] 4,343,996

[45] Aug. 10, 1982

[54] MEDICAL APPARATUS WITH CABLE GUIDE

[75] Inventor: Jan Kuipers, Eindhoven, Netherlands

[73] Assignee: U.S. Philips Corporation, New York, N.Y.

[21] Appl. No.: 866,006

[22] Filed: Dec. 30, 1977

[30] Foreign Application Priority Data

Jul. 7, 1977 [NL] Netherlands ......................... 7707541

[51] Int. Cl.³ ............................................ G03B 41/16
[52] U.S. Cl. ....................................... 378/21; 378/101
[58] Field of Search .................... 250/445 T, 401, 402

[56] References Cited

U.S. PATENT DOCUMENTS 4,099,061  7/1978  Zink ............................... 250/445 T
4,115,696  9/1978  Truscott ......................... 250/445 T Primary Examiner—Craig E. Church
Attorney, Agent, or Firm—Jack E. Haken

[57] ABSTRACT

A cable guide for X-ray scanners includes an elastomer-coated guide roller which rolls between concentric, parallel drums one end of the cable being fastened to one drum and passing around the roller.

1 Claim, 4 Drawing Figures

MEDICAL APPARATUS WITH CABLE GUIDE

The invention relates to a cable guide which comprises a cylindrical inner drum which is rotatable relative to a cylindrical outer drum and a rotatable cylindrical cable guide roller which is disposed between the concentrically disposed drums, the cylinder axis of said roller being parallel to the cylinder axes of the drums, around which roller a flexible cable is passed which near one of its ends is attached to one of the drums.

The term "cylindrical drum" is to be understood in the broadest sense. As will appear from the following description said term is assumed to include also sectors of drums i.e. rotationally asymmetrical bodies which have a similar function. Generally speaking, the term curved guide path might be used.

A cable guide of the type mentioned in the preamble is for example suitable for use in apparatus for X-ray diagnostics and X-ray therapy, for guiding cables which interconnect components which are rotatable relative to each other, the magnitude of the relative rotation generally ranging from a fraction of one revolution to some full revolutions. The cable may comprise both flexible electrical cores as well as flexible cores for conveying gases and liquids.

From British Patent Specification No. 1,127,191 a cable guide of the type mentioned in the preamble is known, in which a plurality of rotatable cable guide rollers are mounted on a carrier which in itself is rotatable about an axis which coincides with the drum axes. When the inner drum and the outer drum are rotated relative to each other, the carrier is driven with the aid of a gear transmission which comprises six slip couplings and six ratchet-wheel couplings. Owing to a specific slippage in the coupling the flexible cable—which is attached both to the inner drum and to the outer drum—is always kept taut during rotation of the drums relative to each other. In the space between the two drums the flexible cable, depending on the relative direction of rotation, is wound from the inner drum onto the cable guide rollers or from the cable guide rollers onto the inner drum, without becoming entangled.

A drawback of the known cable guide described hereinbefore is the comparatively large number of moving parts.

It is an object of the invention to provide a simple cable guide with a minimum of moving parts which are consequently subject to wear.

A cable guide in accordance with the invention is therefore characterized in that the cable guide roller is adapted to roll between the outer surface of the inner drum and the inner surface of the outer drum over geometrical paths which are concentric with the inner drum and the outer drum.

During rotation of the inner drum relative to the outer drum, the cable guide roller thus rolls over the outer surface of the inner drum and over the inner surface of the outer drum, the rolling distances of the cable guide roller measured along the outer surface of the inner drum and the inner surface of the outer drum being equal, the cable which is passed around the cable guide roller rolls from the inner drum to the outer drum or from the outer drum to the inner drum, depending on the direction of rotation relative to each other.

A preferred embodiment of a cable guide in accordance with the invention is characterized in that the outer surface of the cable guide roller is at least partly covered with a layer of an elastic material. Preferably this layer consists of a foam plastic. By lining the cable guide roller with an elastic layer manufacturing tolerances in respect of the outer diameter of the inner drum, the inner diameter of the outer drum and the diameter of the cable guide roller may be comparatively large.

A cable guide in accordance with the invention is particularly suitable for compact incorporation into a medical apparatus with a radiation source which is rotatable relative to a frame, which source is connected to an electrical power supply by means of a flexible cable, so that the invention also relates to medical apparatus comprising such a cable guide.

A particular medical apparatus of this type is characterized in that a movable frame is suspended to the inner drum, in which frame a detector is secured opposite the radiation source mounted in the frame, the central ray of the radiation source intersecting the cylinder axes of the two drums and being parallel to the direction of movement of the frame, whilst the two drums are constituted by sectors of circular cylinders, which have a free area in which the radiation source is movable when the frame is moved relative to the inner drum.

Figure 2:
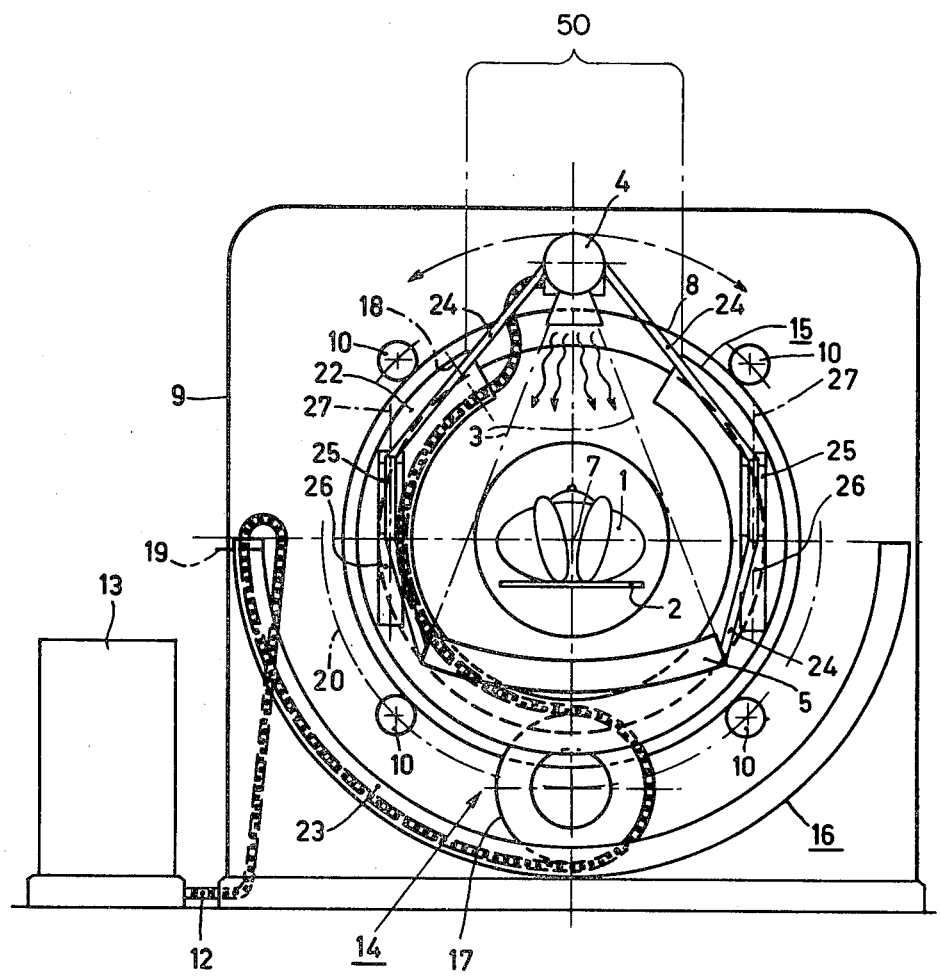
Figure 3:
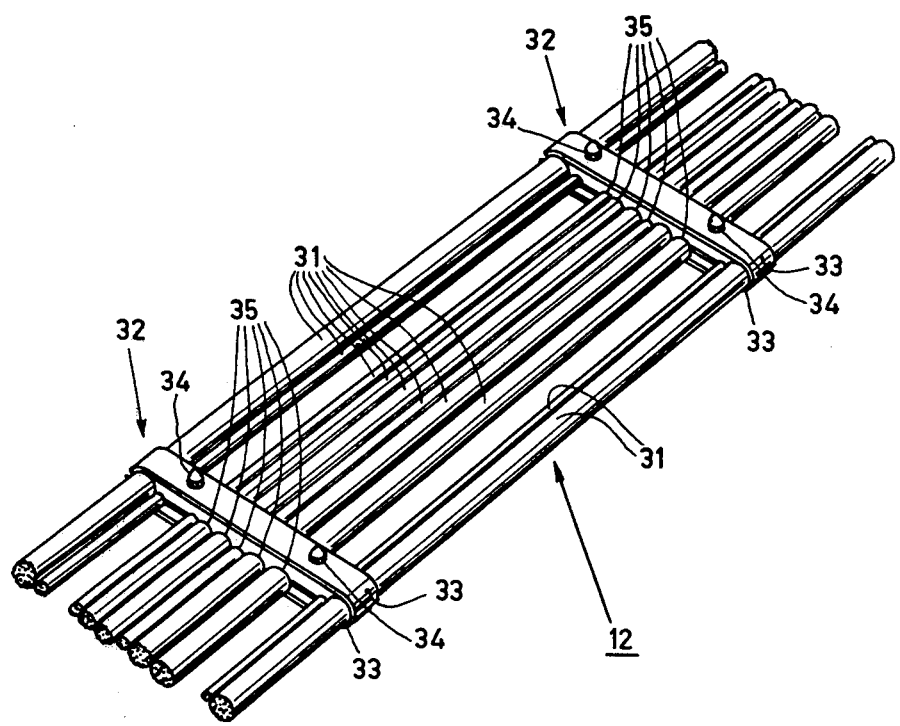
Figure 4:
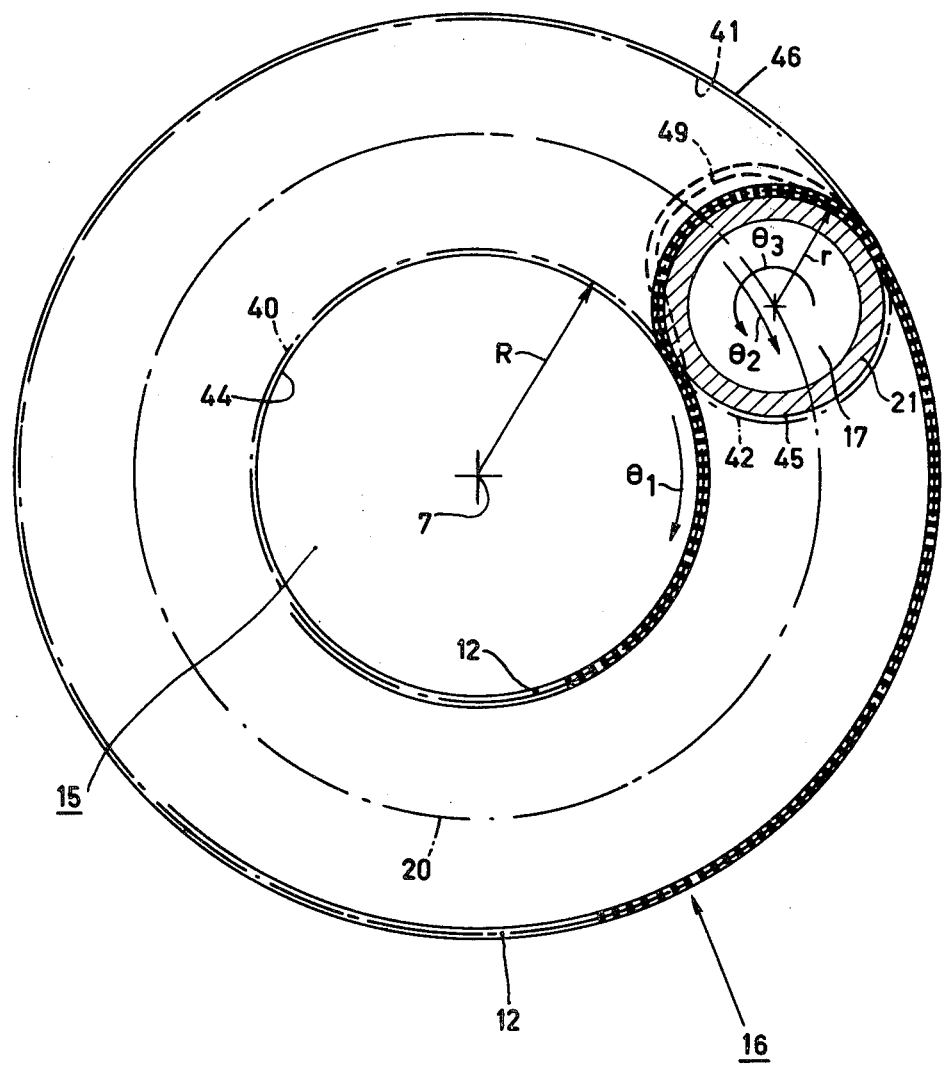

The invention will now be described in more detail with reference to the drawing, which shows an example of a specific application of the cable guide. In the drawing:

FIG. 1 is a longitudinal section of a medical apparatus for computer tomography in accordance with the invention, provided with a cable guide in accordance with the invention, FIG. 2 is a cross-section taken on the line II—II of the apparatus shown in FIG. 1, FIG. 3 shows a flexible multi-core cable which is particularly suitable for use in the cable guide in accordance with FIGS. 1 and 2, and FIG. 4 schematically illustrates a special effect, which a cable guide in accordance with the invention is found to exhibit.

FIG. 1 and FIG. 2 in longitudinal section and cross-section respectively show a medical apparatus for computer tomography, where a patient 1 which is positioned on an examination table 2 is exposed to a planar fan-shaped X-ray beam 3 which is emitted by an X-ray source 4. The radiation transmitted by the patient is measured with an X-ray detector 5, which comprises a series of detection elements 6 which are arranged on an arc of a circle. The X-ray source 4 and the X-ray detector 5 are simultaneously rotated about an axis 7, which is normal to the X-ray beam 3 during examination. With the aid of the computer the density distribution of the patient in the exposed planar slice is computed from the information supplied by the X-ray detector 5. An accurate calculation is possible if the X-ray source 4 and X-ray detector 5 are rotated through an angle of approximately 400°. For this purpose the X-ray source 4 and the X-ray detector 5 are connected to a ring 8 which is journalled on rollers 10 which are arranged in a frame 9 and which is rotatable about the axis 7 with the aid of a drive motor 11.

The X-ray source 4 and the X-ray detector 5 are connected to equipment 13—which inter alia includes a high-voltage supply for the X-ray source—by means of a flexible multicore cable 12, which is accommodated in the frame 9 by a cable guide 14. The cable guide 4 comprises a cylindrical inner drum 15 which is secured to the ring 8, a cylindrical outer drum 16 which is secured to the frame 9, and a cylindrical cable guide roller 17 which is retained between the inner and the outer drum. The inner drum 15 and the outer drum 16 are disposed concentrically and their cylinder axes coincide with the axis 7. The cylinder axis of the cable guide roller 17 is parallel to the axis 7. The cable 12—which is passed around the cable guide roller 17—is attached to the inner drum 15 near an end 18 and to the outer drum 16 near an end 19. During a relative rotation of the inner and outer drum the centre of the cable guide roller 17 moves along a geometrical path 20 which is concentric with the inner and the outer drum. From the following it will be evident that—if the diameter of the inner drum 15 is twice as great as the diameter of the cable guide roller 7—for a 400° rotation of the X-ray source 4 and the X-ray detector 5 about the axis 7 it suffices that the outer drum 16 constitutes half a cylinder (drum) and the inner drum three-quarter of a cylinder (drum).

The cable guider roller 17 is coated with an elastic layer 21, so that manufacturing tolerances in respect of the diameter of the inner drum 15, the outer drum 16 and the cable guide roller 17 may be comparatively large. The inner drum 15 and the outer drum 16 are provided with circular flanges 22 and 23 respectively, between which the cable guide roller 17 is guided, so that the tolerances during alignment of the cylinder axes of the inner and the outer drum relative to each other may be comparatively large. The flexible cable 12 is retained between the outer surface of the inner drum 15, the outer surface of the cable guide roller 17 which is provided with an elastic coating 21, and the inner surface of the outer drum 16. It has been found that this method of retaining the cable has a stabilizing effect on the operation of the cable guide. It has appeared that in the case that the cable guide roller—owing to whatever cause—is not disposed entirely within the cable loop a so-called "creeping-effect" occurs during the movement of the cable guide roller, so that the roller has always returned into the cable loop, after some time. The suspected cause of said "creeping-effect" will be further discussed on the basis of angular rotation equations and with reference to FIG. 4.

The X-ray source 4 and the X-ray detector 5 are secured to a frame 24 which by means of slides 25 is movable in guides 26 which are mounted on the inner drum 15. The slides 25—which may for example be driven by an electric motor in a manner known per se, are movable in a direction 27, perpendicular to the axis 7. By moving the frame 24 relative to the patient 1, the size of the patient area to be examines can be changed (geometrical magnification). When all detection elements 6 then remain in use, the accuracy with which the density distribution can be calculated will increase when the examined patient area is reduced and will decrease when said area is enlarged. This freedom of changing the accuracy of the density distribution calculation at option is of great significance in computer tomography.

FIG. 3 shows a flexible cable 12, which contains ten adjacent cores 31. The cores 31 are retained—viewed in the longitudinal direction of the cable—by means of regularly spaced clamps 32 which extend transversely to the longitudinal direction of the cable. The clamps 32 comprise two parts 33 which are clamped around the cable cores with the aid of screws 34. The parts 33 of the clamps 32 are provided with beds 35 which are dimensioned so that the centres of the cores 31—viewed in a cross-section at the location of the clamps—are disposed on a straight line which is substantially parallel to the axis of rotation 7. Such an arrangement prevents unequal mechanical loading of the different cores. The set of such straight lines, which is obtained by taking all cross-sections of the cable, constitutes the so-called neutral plane of mechanical loading of the bent cable. The centre lines of the individual cores are disposed substantially in this curved plane. In order to explain the operation of the cable guide angular rotation equations will be derived hereinafter (see FIG. 4).

The relative angular rotation about the axis 7 of the inner drum 15 relative to the outer drum 16 is designated $\theta_1$. In the present example with a stationary outer drum 16 $\theta_1$ consequently equals the absolute angular rotation of the inner drum 15 about the axis 7. The cable guide roller is represented by a circle 42 of a radius r, whilst the inner drum is represented by a circle 40 of radius R. The radii r and R are related to the said neutral plane of the cable 12. The flexible cable 12 is retained between the outer surface 44 of the inner drum 15, the outer surface 45 of the cable guide roller 17, and the inner surface 46 of the outer drum 16. In the case of a relative rotation $\theta_1$, the cable guide roller 17 rolls over the outer surface 44 of the inner drum 15 and over the inner surface 46 of the outer drum 16. The cable 12 which is passed around the cable guide roller 17 then rolls from the inner drum 15 to the outer drum 16 or vice versa depending on the direction of rotation. The angular rotation of the centre of the cable guide roller 17 relative to the axis 7 upon displacement over the geometrical path 20 is designated $\theta_2$ and the angular rotation of the cable guide roller about its own axis by $\theta_3$. For a rotation $\theta_1$ of the inner drum 15 relative to the outer drum 16—in the direction indicated in FIG. 4—a length of cable $\theta_2 \cdot (R+2r)$ is unrolled from the outer drum 16. Said length is equal to the cable length $\theta_3 \cdot r$ which is transmitted by the cable guide roller 17 and to the cable length $(\theta_1-\theta_2) \cdot R$ which is rolled onto the inner drum 15. It follows that:

$$\theta_2 \cdot (R+2r) = \theta_3 \cdot r = (\theta_1 - \theta_2) \cdot R$$

and $$\theta_2 = \frac{R}{2(R+r)} \cdot \theta_1.$$

These equations remain valid in the case of rotation in a direction opposite to that indicated in FIG. 4.

From the equation it is evident that a relative rotation $\theta_1$ of 400°—as was desired for the computer tomography apparatus shown in FIG. 1 and FIG. 2—causes a rotation $\theta_2$ of 133° of the cable guide roller 17 over the geometrical path 40 if R=2r. For this rotation the inner drum 15 should take up a cable length (400-133) $1/2\pi \cdot R$. In the present example it therefore suffices that the outer drum 16 has the shape of half a cylinder and the inner drum 15 of three quarter of a cylinder.

It is suspected that if the cable guide roller 17 is coated with an elastic layer 21, said layer is depressed by the cable 12 owing to the rigidity of the cable, when the direction of rotation $\theta_1$ is opposed to the direction of rotation indicated in FIG. 4. The cable 12 then extends as is shown exaggerated by the reference numeral 49. This means that the effective diameter of the cable guide roller 17 then decreases and that the effective diameter of the inner drum 15 increases. If said decrease or increase is assumed to be $\Delta$, the following equation is valid—indicated by an accent—for the rotation of the cable guide roller 17:

$$\theta'_2 = \frac{R + \Delta}{2(R + \Delta + r - \frac{1}{2}\Delta)} \cdot \theta_1, \text{ so that } \theta'_2 > \theta_2.$$

so that $\theta_2' > \theta_2$.

Thus it is apparent from the formula that in the case of rotation of the drums 15 and 16 relative to each other in a direction opposite to the direction indicated in FIG. 4, the cable guide roller 17 rotates along faster with the inner drum 15 than in the case of a relative rotation in the direction indicated in FIG. 4. This would mean that the cable guide roller 17 in fact continually searches for the loop in the cable 12 (creeping effect), which has a stabilizing effect on the operation of the cable guide.

In a preferred embodiment of a medical apparatus in accordance with the invention as shown in the FIGS. 1 and 2, use is made of the previously mentioned fact that the inner drum need only constitute three quarter of a cylinder and the outer drum half a cylinder. The axis of symmetry of the frame 24 passes through the centre of the circular sectors and the X-ray source may thus move into the free area 50 defined by the openings in the cylinders. These sectors are utilized when the X-ray source 4 is moved towards the axis 7, for changing the geometrical enlargement. Thus, the previously discussed and highly desirable freedom is obtained of adapting the accuracy of the density of distribution calculation.

It is to be noted that by the use of a sectoral inner drum and a sectoral outer drum, a comparatively flat construction (see FIG. 1) is obtained.

The cable guide in accordance with the invention is by no means limited to medical apparatus for computer tomography, although it yield special advantages in this application. In the commonly known so-called angular medical stands the cable guide in accordance with the invention also yields the advantage of easy integration with the rest of the construction, so that the compactness of the assembly is increased thereby. The use of the cable guide in accordance with the invention is neither limited to medical apparatus. In general, the cable guide may be used in those cases where energy is to be transmitted through cables between relatively rotatable parts. This energy may be electrical, pneumatic as well as hydraulic.

What is claimed is:

1. Medical apparatus comprising:
   an X-ray radiation source which is rotatable relative to a fixed frame;
   an electrical power supply;
   a flexible cable connecting the source to the power supply;
   a guide for the flexible cable, including a cylindrical inner drum, a cylindrical outer drum disposed concentric to and rotatable relative to the cylindrical inner drum, a rotatable cylindrical cable guide roller disposed between the concentrically disposed drums, the axis of the roller being parallel to the axes of the drums, the flexible cable passing around the roller, the cable being attached near one of its ends to one of the drums, the cable guide roller being retained between an outer surface of the inner drum and an inner surface of the outer drum and being positioned to roll along geometrical paths which are concentric with the inner drum and the outer drum;
   an elastic material which is disposed on and at least partially covers the surface of the cable guide roller and which functions to stabilize the operation of the guide;
   a second movable frame suspended on the inner drum and movable, with respect thereto, in a direction perpendicular to the axis of the drums, in which frame the radiation source is mounted;
   a detector secured on the movable frame opposite the radiation source, a central ray from the radiation source intersecting the axes of the two drums and being parallel to the direction of movement of the frame;
   wherein each of the two drums is shaped as a sector of a circular cylinder and includes a sector-shaped opening, the two openings being angularly aligned to define a free area, the radiation source being movable into the free area when the frame is moved relative to the inner drum.

* * * * *